(12) United States Patent
Bouchard et al.

(10) Patent No.: US 6,689,114 B2
(45) Date of Patent: Feb. 10, 2004

(54) SANITARY NAPKIN AND METHOD FOR COLLECTING SAMPLES OF BODILY SUBSTANCES

(75) Inventors: Céline Bouchard, Sillery (CA); Carol Morin, Quebec (CA); Michel Fortier, Sillery (CA)

(73) Assignee: Ezy-Detek (EDI, Inc.), Sillery, CA (US)

(*) Notice: Subject to any disclaimer, the term of this patent is extended or adjusted under 35 U.S.C. 154(b) by 5 days.

(21) Appl. No.: 09/804,102

(22) Filed: Mar. 12, 2001

(65) Prior Publication Data

US 2001/0011167 A1 Aug. 2, 2001

Related U.S. Application Data

(62) Division of application No. 09/258,950, filed on Mar. 1, 1999, which is a continuation of application No. 08/668,894, filed on Jun. 24, 1996, now Pat. No. 5,876,389.

(51) Int. Cl.[7] .............................. A61F 13/15; A61B 5/00
(52) U.S. Cl. .................................. 604/385.14; 600/573
(58) Field of Search ............................... 604/361, 362, 604/385.05, 385.06, 385.11, 385.14; 600/573–575

(56) References Cited

U.S. PATENT DOCUMENTS

| | | | |
|---|---|---|---|
| RE24,666 E | 7/1959 | Draghi | |
| 2,894,511 A | 7/1959 | Devaud | |
| 2,929,379 A | 3/1960 | Poulson | |
| 3,704,710 A | 12/1972 | Fifer | |
| 3,731,685 A | 5/1973 | Eidus | |
| 3,850,160 A | 11/1974 | Denson | |
| 3,867,924 A | 2/1975 | Bucalo | |
| 3,918,433 A | * 11/1975 | Fuisz | 600/573 |
| 4,072,150 A | 2/1978 | Glassman | |
| 4,114,621 A | 9/1978 | Mims, Jr. | |
| 4,444,193 A | 4/1984 | Fogt et al. | |
| 4,605,404 A | 8/1986 | Sneider | |
| 4,789,629 A | 12/1988 | Baker et al. | |
| 4,806,408 A | 2/1989 | Pierre et al. | |
| 4,808,379 A | 2/1989 | Wardlaw et al. | |
| 5,088,502 A | 2/1992 | Miller | |
| 5,119,828 A | 6/1992 | Miller | |
| 5,231,992 A | 8/1993 | Leon | |
| 5,300,358 A | 4/1994 | Evers | |
| 5,429,631 A | 7/1995 | Grenier | |
| 5,432,097 A | 7/1995 | Yourno | |
| 5,817,012 A | 10/1998 | Schoendorfer | |
| 5,823,953 A | * 10/1998 | Roskin et al. | 600/309 |
| 5,876,389 A | 3/1999 | Bouchard et al. | |
| 5,899,856 A | 5/1999 | Schoendorfer et al. | |
| 6,106,461 A | 8/2000 | Roskin et al. | |

FOREIGN PATENT DOCUMENTS

| | | |
|---|---|---|
| DE | 3810473 | 10/1989 |
| FR | 2 399 231 | 3/1979 |
| FR | 2 599 500 | 12/1987 |
| GB | 520576 | 4/1940 |
| WO | 91/19471 | 12/1991 |
| WO | 94/10958 | 5/1994 |

* cited by examiner

*Primary Examiner*—Weilun Lo
*Assistant Examiner*—C. Lynne Anderson
(74) *Attorney, Agent, or Firm*—Calfee, Halter & Griswold, LLP

(57) ABSTRACT

A method of collecting bodily substances from a subject, comprising the steps of (a) positioning a member in an undergarment; (b) collecting at least one bodily substance from the genital, anal, or urinary regions from the subject on the sampling strip; and (c) removing the sampling strip from the member for analysis of the bodily substances collected thereon. The member comprises a sleeve, a sampling strip, and an absorbent layer. The sleeve comprises upper and lower sheets and is at least partially open ended at one longitudinal end. The upper sheet of the sleeve at least partially comprises a receiving surface, and the lower sheet has an impermeable outer surface with an adhesive thereon for securing the member to the subject's undergarments. The sampling strip is between the absorbent layer and the receiving surface and is removable from the sleeve through the opening at one longitudinal end.

1 Claim, 1 Drawing Sheet

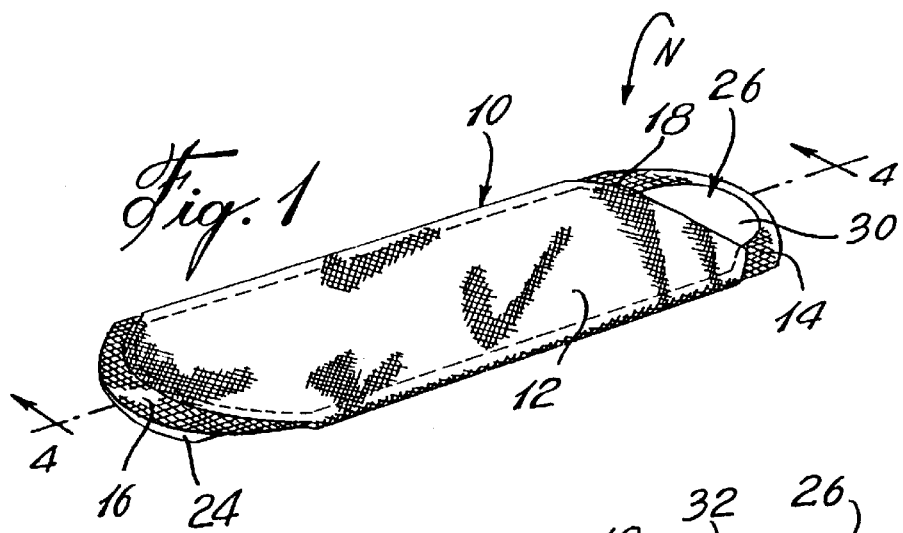
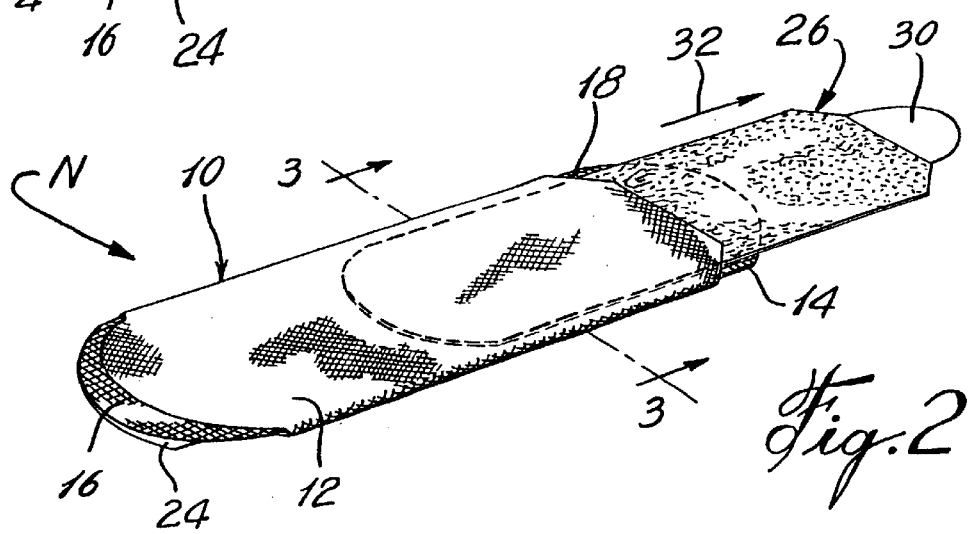
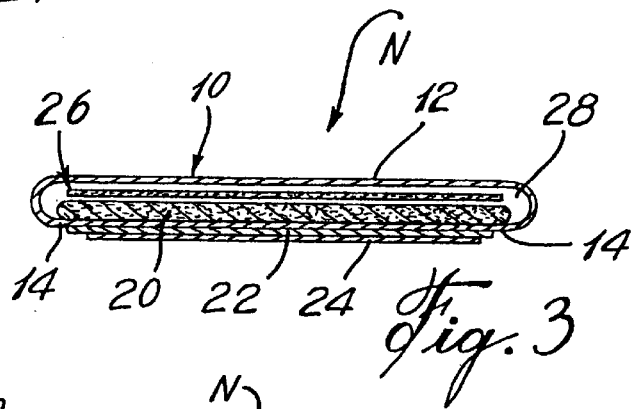
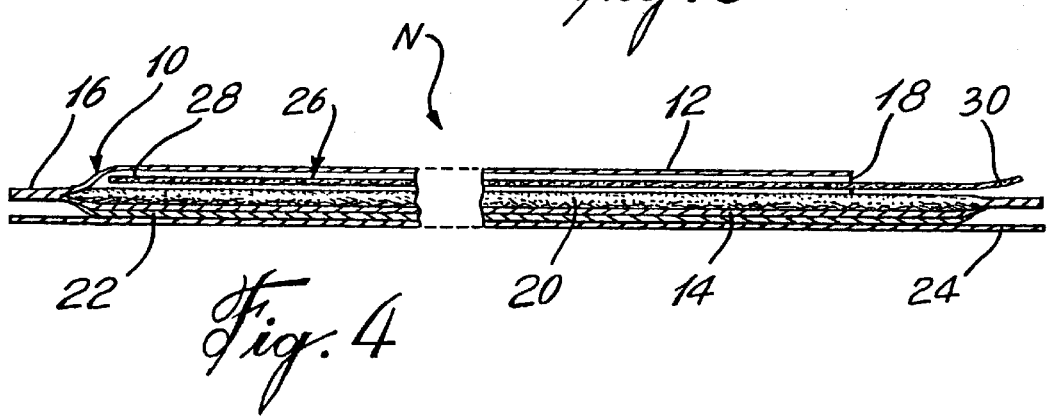

SANITARY NAPKIN AND METHOD FOR COLLECTING SAMPLES OF BODILY SUBSTANCES

CROSS-REFERENCE TO RELATED APPLICATIONS

This application is a divisional of the co-pending, commonly assigned, U.S. patent application Ser. No. 09/258,950, filed Mar. 1, 1999, which is a continuation of U.S. patent application Ser. No. 08/668,894 filed on Jun. 24, 1996, which issued as U.S. Pat. No. 5,876,389 on Mar. 2, 1999.

BACKGROUND OF INVENTION

1. Field of the Invention

The present invention relates to collection devices for recovering samples of bodily fluids or cells for subsequent laboratory analysis and, more particularly, to a collection device and method for allowing the patient to recover samples of bodily fluids, secretions, cells, and infectious and noninfectious agents, in whole all hereinafter referred to as bodily substances, and, for instance, to a modified sanitary napkin for collecting such substances from the genital, anal or urinary regions, and to a method associated with the use thereof.

2. Description of Prior Art

U.S. Pat. No. 5,231,992 issued on Aug. 3, 1993 to Leon discloses a low-impact cervical cell and fluid collector which includes a substantially disc-shaped main body 12 which defines a generally concave recess 14 into which a porous collection membrane 16 is mounted. Therefore, when the collector 10 is in place adjacent to the patient's cervix, cells and fluids adhere to the outer surface of the membrane 16. Underneath the membrane 16, there is provided a layer 24 of a cell-moistening material or agent, such as a polymer gel adapted to release water during cell collection for moistening collected cells through the pores of the membrane 16 when the cells are adhered to the outer surface thereof. The main body 12 can be provided with a string 18 to facilitate the removal of the collector 10 from the body.

French Patent Application which was published as FR-2 599 500 on Dec. 4, 1987 in the name of Chieusse discloses a transparent adhesive strip for taking a sample directly from the skin's surface for microscopic examination or analysis, the adhesive strip comprising a rigid transparent resin or glass plate 1 covered successively with a transparent layer 2 which is self-adhesive on both of its sides, an isolating film or coating 4 of shorter length, and a semi-rigid cover layer 3 made, for instance, of strong paper or cardboard. The limited length of the film 4 defines a section 5 where the cover layer 3 adheres directly to the adhesive 2 and forms a joint line 6 which allows for the cover layer 3 to be pivotally lifted about the hinge 6, wherein in a closed position 7, the sample-taking surface 9 is protected for its transport or storage, whereas in its open position 8, the adhesive surface 2 can be brought into direct contact with the skin's surface such as to enable the adhesive strip 2 to remove and collect desired samples from the skin and other surfaces for subsequent analysis thereof.

U.S. Re-Issue Pat. No. RE 24,666 issued on Jul. 7, 1959 to Draghi discloses a tampon for the detection of cancer of the pelvic region. More particularly, the tampon of this U.S. patent constitutes a preliminary diagnosis method which determines if there are present any indicia of cancer by taking a sample of cells which are present in the cervical canal and in the vagina and by the subsequent microscopic analysis of these cells. The tampon includes a tampon body 10 partly covered by a jacket 12 terminating with an enlarged cap 13 and, at the other end of the tampon body 10, there is provided a string 22. The assembly of the body 10 and jacket 12 forms a detection tampon 14. The enlarged cap 13 which closes one end of the tampon 14 is adapted to extend farthest into the vaginal canal and to collect and retain in moist form cells thereof. The jacket 12 also collects cells and retains them in a relatively moist condition thereby ensuring a more accurate clinical evaluation.

U.S. Pat. No. 3,850,160 issued on Nov. 26, 1974 to Denson discloses a diagnostic tampon 10 having a supporting body 13 covered by an outer film 12 and provided at one end thereof with a removal string 11. The tampon is particularly adapted for collecting cellular material from body cavities, in particular from the vaginal cavity, for subsequent examination.

U.S. Pat. No. 5,432,097 issued on Jul. 11, 1995 to Yourno teaches a method for the recovery of blood cells from dried blood spots on a filter paper.

U.S. Pat. No. 5,119,828 issued on Jun. 9, 1992 to Miller discloses a device 10 for collecting sebum which is secreted by the sebaceous glands of a patient, the device 10 including a microporous film 12 which is opaque to light when the pores are filled with gaseous material and which is substantially translucent when the film pores are filled with sebum. The film 12 is mounted to a substrate 14 which defines a light absorbing area 16 for enhancing visualization of the pores of the film 12 when filled with sebum. In use, the device is pressed against the patient's skin surface such that the film 12 contacts the skin and absorbs its sebum, whereby a sebum spot pattern is developed in the film 12 and is visually enhanced by way of the light absorbing area 16.

U.S. Pat. No. 5,088,502 issued on Feb. 18, 1992 to Miller discloses a device 10 for sampling the surface of the skin which includes a substrate 12 having a light absorbing area 14 disposed thereon with an adhesive layer 16 being disposed on the substrate 12 such as to overlie the light absorbing area 14. The adhesive layer 16 is optically clear and under pressure conforms to the surface of the skin to be sampled. A removable protective film 18 provided with a tab 20 is disposed on the adhesive layer 16 for protecting the same prior to use of the device. The device and, more particularly, the adhesive layer 16 is placed against the skin surface such that, when removed, skin cells adhere to the adhesive layer 16. The sampled cells can then be visualized in view of the light absorbing area 14.

U.S. Pat. No. 4,789,629 issued on Dec. 6, 1988 to Baker et al teaches a device for collecting and testing fecal occult blood which includes a pocket-like member 16 and an absorbent insert 24 disposed in the pocket member 16. The pocket member 16 is disposed on the inside front cover of the device such that when the cover is in a closed position thereof, the pocket 16 overlies the fecal smear on the specimen receiving sheet 36, whereby with one single collection, two separate membranes, that is the specimen receiving sheet 36 and the absorbent insert 24, receive the components of the fecal sample and can be individually and independently tested.

U.S. Pat. No. 4,808,379 issued on Feb. 28, 1989 to Wardlaw et al discloses a device for obtaining stool samples and detecting occult blood and which is used in a way similar to toilet tissue to obtain a stool sample on a receptor sheet 26 provided in the device. Therefore, to obtain the stool sample, the patient, after defecation, draws the cover sheet 32 and its holes 34 across the rectum in the same manner as toilet tissue such that stool is thus wiped onto the cover sheet and passes through the openings 34 and deposits in spots on the receptor sheet 26. The cover sheet 32 is then peeled off and discarded, thereby exposing the stool spots S of the receptor sheet 26, after which the stool spots S can be effectively sealed in the device by folding the impermeable sheet 2.

SUMMARY OF INVENTION

It is therefore an aim of the present invention to provide an improved device for allowing a patient to collect externally from the body samples of bodily substances, such as fluids, cells, tissues, microorganisms, etc.

It is also an aim of the present invention to provide an improved method for allowing a patient to collect externally from the body samples of bodily substances, such as fluids, cells, tissues, microorganisms, etc.

It is a further aim of the present invention to provide a modified sanitary napkin for collecting samples of bodily substances from the genital, anal or urinary regions and, for instance, vaginal secretions.

It is a still further aim of the present invention to provide a modified sanitary napkin provided with an absorbent layer for collecting the samples of bodily substances from the genital, anal or urinary regions.

It is a still further aim of the present invention to provide a collection device, such as a modified sanitary napkin, having a removable collection strip, membrane or filter, in particular in the form of an absorbent strip, slidably received in a pocket defined in the collection device or sanitary napkin.

Therefore, in accordance with the present invention, there is provided a collection device for collecting bodily substances from the genital, anal or urinary regions, comprising a substantially flexible and comfortable member adapted to be positioned such that a receiving surface of said member is located substantially opposite a location from which a sample of bodily substance is to be taken, collecting means in said member and in communication with said receiving surface, whereby sufficient bodily substance contacting said receiving surface is at least partly collected by said collecting means for subsequent analysis thereof.

Also in accordance with the present invention, there is provided a collection device for allowing a user to collect bodily substances, comprising a member adapted to be externally worn by the user such that a receiving surface of said member is located substantially opposite a location of the user at which a sample of bodily substance is to be taken, collecting means in said member and in communication with said receiving surface, said collecting means being removable from said member by the user, whereby once sufficient bodily substance having contacted said receiving surface has been at least partly collected by said collecting means, said collecting means is removed from said member for subsequent analysis thereof.

Further in accordance with the present invention, there is provided a method of self-collection of bodily substances, comprising the steps of:
 (a) self-positioning collector means externally on a user and at a location of the user at which a sample of bodily substance is to be taken; and
 (b) collecting on said collector means at least one bodily substance from the user.

BRIEF DESCRIPTION OF THE DRAWINGS

Having thus generally described the nature of the invention, reference will now be made to the accompanying drawings, showing by way of illustration a preferred embodiment thereof, and in which:

FIG. 1 is a perspective view of a modified sanitary napkin in accordance with the present invention;

FIG. 2 is a perspective view of the sanitary napkin of FIG. 1 but illustrated with its removable absorbent sampling strip partly removed therefrom;

FIG. 3 is a transversal cross-sectional view taken along line 3—3 of FIG. 2; and FIG. 4 is a longitudinal cross-sectional view taken along line 4—4 of FIG. 1.

DESCRIPTION OF THE PREFERRED EMBODIMENTS

The present invention is concerned with the collection of samples of bodily substances (such as fluids, secretions, cells, microorganisms, infectious and non-infectious agents, etc.) and, more particularly, in view of some people's reticence in having these samples taken at a clinic or hospital, with a collection device and method which allow the patient to "self-collect" the samples, typically outside of any formal medical environment, which can then be properly packaged and forwarded for subsequent analysis thereof to any appropriate medical facility, e.g. laboratory.

In the present description as well as in the appended claims, the terms "substance" and "substances" are understood to include any bodily fluids, secretions, cells, microorganisms, infectious and noninfectious agents, etc., which can be externally recovered from the body.

For instance, and in accordance with the present invention, FIG. 1 illustrates a modified sanitary napkin N which is intended for collecting substances at the genital and anal regions and which includes a porous outer sleeve 10 having upper and lower sheets 12 and 14, respectively, which are joined at a first longitudinal end 16 thereof and which are open at an opposite second longitudinal end 18 of the sleeve 10. The upper and lower sheets 12 and 14 are at least partly made of a porous fabric, typically in the form of a close knit netting. Inside the sleeve 10, there is provided an absorbent layer 20, of the type well known in the art of sanitary napkins. The absorbent layer 20 is peripherally secured to the upper and lower sheets 12 and 14 of the porous sleeve 10, apart from at the second end 18 where the absorbent layer 20 is typically only secured to the lower sheet 14 such that the opening at the second end 18 is defined between the upper sheet 12 and the absorbent layer 20, as best seen in FIG. 4.

Under or outwardly of the lower sheet 14, an insulating or impermeable layer 22 acting as a liquid impervious barrier is mounted to the lower sheet 14 and is provided with an adhesive coating on a side of the impermeable layer 22 opposite its side secured to the lower sheet 14 of the sleeve 10. A removable strip 24 is detachably mounted to the adhesive coating of the impermeable layer 22 such that it can be removed therefrom when the sanitary napkin N is to be attached to an undergarment.

Intermediate the upper sheet 12 of the sleeve 10 and the absorbent layer 20, a removable absorbent sampling filter or strip 26 is slidably received in a pocket 28 which is defined between the upper sheet 12 and the absorbent layer 20 and which is open at the second end 18, again as best seen in FIG. 4. The sampling strip 26 is provided at an outside end thereof with a handling tab 30. The sampling strip 26 can be made, for instance, of a semi-porous and absorbent material, e.g. a sheet-like filter made of paper, of synthetic or non-synthetic fabrics, etc., such as to allow the patient to collect substances, for instance vaginal secretions, as samples for subsequent analysis thereof in a laboratory or the like while allowing for excess secretions and fluids to pass therethrough and reach the absorbent layer 20 and to be collected thereon.

In the present embodiment of the invention which takes the form of the sanitary napkin N, the description might refer to vaginal secretions instead of the more general "substances" mentioned hereinabove, but this is only done for illustration purposes, that is as an example of a use of the present sanitary napkin N and is obviously not intended to restrict the scope of use of any collection device in accordance with the present invention to the single collection of vaginal secretion samples.

More particularly, in use, the sanitary napkin N has the form generally shown in FIG. 1 with its removable strip 24 being removed therefrom such as to allow the sanitary napkin N to be attached to an undergarment. Subsequently, vaginal secretions, for example, will come into contact with the sanitary napkin N and, more particularly, with the upper sheet 12 of the sleeve 10 thereof. Through the netting of the upper sheet 12, the vaginal secretions will then reach the sampling strip 26, whereat some of the secretions will be absorbed and retained by the sampling strip 26 with the remainder of the secretions filtering therethrough and reaching the absorbent layer 20. Therefore, a sampling of vaginal secretions will have collected on the sampling strip 26 which, before the sanitary napkin N is discarded, is removed from the sanitary napkin N as per arrow 32 of FIG. 2, whereby the sampling strip 26 can then be properly packaged and sent, for instance, to a laboratory to be analyzed.

Therefore, the sanitary napkin N of the present invention which is intended to facilitate and render more accessible the uncovering, for example, of sexually transmitted diseases by reducing some people's resistance to showing up at clinics to be tested by way of the collection of samples for analysis purposes, is considered to meet this object as, clearly, the simple use in a typically well-known fashion of a substantially recognizable sanitary napkin N will allow for a proper sampling of bodily substances, such as vaginal secretions, to be easily obtained and forwarded to a laboratory, using the present absorbent sampling strip or filter 26 as a collection medium which is typically sealed in an appropriate container once it has been removed from the sanitary napkin N, and until it is ready to be analyzed in the laboratory.

In the laboratory, the sampling filter 26 can be analyzed by way of known techniques, such as polymerase chain reaction (PCR) and ligase chain reaction (LCR) techniques, etc.

Accordingly, the present sanitary napkin N which is based on modifications made to conventional sanitary napkins can be easily used by the patient as a collection and reception medium for various substances (e.g. secretions) provided externally of the genital, anal or urinary regions, from which a sample can then be obtained by removing the sampling strip 26 from the sanitary napkin N.

The present invention also contemplates having a non-removable, i.e. at the level of the end user, sampling filtering strip or collector installed in the sanitary napkin, whereby the complete sanitary napkin would be sent to the laboratory, whereat it would be appropriately dismantled to retrieve its sampling strip for the analysis thereof.

Furthermore, by the present invention, there is also provided a method of collecting samples of bodily substances, such as of secretions emitted at the genital, anal or urinary regions, by providing a collection medium which is adapted to be positioned at an appropriate location, for instance in the undergarment, and externally of the user, and which is further adapted to receive and/or collect samples of bodily substances, the samples being then typically properly packaged for the subsequent analysis thereof.

The present collection device, which has been herein preferably shown and described in the form of the sanitary napkin N for collecting vaginal secretions, as well as the present collection method can obviously be also used to collect various other bodily substances, such as biological fluids, blood, tissues, microorganisms or cells (again all herein generally referred to as substances), for instance, from the genito-urinary tract or system and/or from the anal region.

Accordingly, various applications of the collection device are foreseen, such as (1) for the analysis of products accumulated in the collector filter or sampling strip 26, including research on and identification of infectious agents (e.g. chlamydia, HIV, gonorrhea, herpes, cytomegalovirus, human papillomavirus, mycoplasma, ureaplasma, candida and other infectious and non-infectious agents, etc.) or parasites (e.g. trichomonas) or any other biochemical particle or component originating from these agents with a view of identifying and treating these agents by known techniques as well as by techniques which will be developed; (2) for the analysis of cells from the genito-urinary or intestinal system for the chromosomal, histological, cytological, biochemical or biomolecular analysis thereof; (3) for the analysis of the menstrual blood, or its derivatives (e.g. antibodies) and of any other molecule detected in the sampling strip 26; (4) for the analysis of urine, of its derivatives and of any other molecule originating from the urinary system and detected in the sampling strip 26; and (5) for the analysis of products derived from the pilosebaceous system of the genital, anal and cutaneous sphere; etc.

Basically, the invention is intended to enable the patient to recover samples of secretions, fluids, etc. emitted from the body, as well as samples of cells, fluids, etc. which are present at the cutaneous level (e.g. for the collection of substances from sores, etc., such as in the case of some types of herpetic infections which manifest on the skin) and to sealingly package the collected samples which can then be forwarded to a laboratory for the analysis thereof.

We claim:

1. A method of collecting bodily substances from a subject, comprising the steps of:

(a) positioning a member in an undergarment for collecting substances from the genital, anal or urinary regions of the subject, said member comprising a sleeve, a sampling strip, and an absorbent layer;

wherein said sleeve comprises upper and lower sheets, said upper sheet being at least partly comprised of a receiving surface, said lower sheet having an impermeable outer surface with an adhesive thereon for securing said member to the undergarment, and a protective removable strip being provided outwardly on said adhesive;

wherein said sleeve is at least partly open ended at one longitudinal end thereof;

wherein said absorbent layer is in said sleeve;

wherein said sampling strip is removably received in said sleeve through said one end such as to be removable from said sleeve;

wherein said sampling strip is between said absorbent layer and said receiving surface, and wherein said receiving surface is adapted to allow bodily substances to reach said sampling strip;

(b) collecting on said sampling strip at least one bodily substance from the subject, and (c) removing said sampling strip from said member for analysis of the bodily substances collected on said sampling strip.

* * * * *